US011756161B2

(12) United States Patent
Hu et al.

(10) Patent No.: US 11,756,161 B2
(45) Date of Patent: Sep. 12, 2023

(54) METHOD AND SYSTEM FOR GENERATING MULTI-TASK LEARNING-TYPE GENERATIVE ADVERSARIAL NETWORK FOR LOW-DOSE PET RECONSTRUCTION

(71) Applicant: SHENZHEN INSTITUTES OF ADVANCED TECHNOLOGY, Guangdong (CN)

(72) Inventors: Zhanli Hu, Guangdong (CN); Hairong Zheng, Guangdong (CN); Na Zhang, Guangdong (CN); Xin Liu, Guangdong (CN); Dong Liang, Guangdong (CN); Yongfeng Yang, Guangdong (CN); Hanyu Sun, Guangdong (CN)

(73) Assignee: SHENZHEN INSTITUTES OF ADVANCED TECHNOLOGY, Guangdong (CN)

( * ) Notice: Subject to any disclaimer, the term of this patent is extended or adjusted under 35 U.S.C. 154(b) by 299 days.

(21) Appl. No.: 17/340,117

(22) Filed: Jun. 7, 2021

(65) Prior Publication Data
US 2022/0188978 A1 Jun. 16, 2022

Related U.S. Application Data

(63) Continuation of application No. PCT/CN2020/135332, filed on Dec. 10, 2020.

(51) Int. Cl.
*G06T 5/00* (2006.01)
*A61B 6/03* (2006.01)
(Continued)

(52) U.S. Cl.
CPC .............. *G06T 5/00* (2013.01); *A61B 6/037* (2013.01); *G06N 3/045* (2023.01); *G06N 3/08* (2013.01);
(Continued)

(58) Field of Classification Search
CPC ............ G06T 5/00; G06T 2207/10088; G06T 2207/10104; G06T 2207/20081;
(Continued)

(56) References Cited

U.S. PATENT DOCUMENTS

2019/0035118 A1* 1/2019 Zhao ..................... G06T 11/008
2019/0049540 A1* 2/2019 Odry .................... G01R 33/543
(Continued)

OTHER PUBLICATIONS

Ryohei Kuga et al., "Multi-task Learning Using Multi-modal Encoder-Decoder Networks with Shared Skip Connections," 2017 IEEE International Conference on Computer Vision Workshops (ICCVW), Oct. 22-29, 2017, pp. 403-411. (Year: 2017).*
(Continued)

*Primary Examiner* — Van D Huynh

(57) ABSTRACT

The present application relates to a method and system for generating multi-task learning-type generative adversarial network for low-dose PET reconstruction, and relates to the field of deep learning. The method includes connecting layers of the encoder with layers of the decoder by skip connection to provide a U-Net type picture generator; generating a group of generative adversarial networks by matching a plurality of picture generators with a plurality of discriminators in one-to-one manner; obtaining a first multi-task learning-type generative adversarial network; designing a joint loss function 1 for improving image quality; and training the first multi-task learning-type generative adversarial network according to the joint loss function 1 in combination with an optimizer to provide a second multi-task learning-type generative adversarial network.

8 Claims, 4 Drawing Sheets

(51) Int. Cl.
  *G06N 3/08* (2023.01)
  *G06N 3/045* (2023.01)
(52) U.S. Cl.
  CPC ............... *G06T 2207/10088* (2013.01); *G06T 2207/10104* (2013.01); *G06T 2207/20081* (2013.01)
(58) Field of Classification Search
  CPC . G06T 5/50; G06T 5/001; G06T 2207/20084; A61B 6/037; G06N 3/045; G06N 3/08; G06N 3/088
  USPC .......................................................... 382/131
  See application file for complete search history.

(56) References Cited

U.S. PATENT DOCUMENTS

| | | | |
|---|---|---|---|
| 2019/0371450 A1* | 12/2019 | Lou ........................ | G16H 20/40 |
| 2020/0118306 A1* | 4/2020 | Ye ......................... | G06T 11/008 |
| 2020/0126231 A1* | 4/2020 | Hu ......................... | G06T 7/0016 |
| 2020/0311914 A1* | 10/2020 | Zaharchuk ............. | G06N 20/10 |
| 2020/0342306 A1* | 10/2020 | Giovannini .............. | G06N 3/08 |
| 2021/0232860 A1* | 7/2021 | Liu ........................ | G06F 18/214 |

OTHER PUBLICATIONS

Kevin T. Chen et al., "Ultra-Low-Dose 18F-Florbetaben Amyloid PET Imaging Using Deep Learning with Multi-Contrast MRI Inputs," Radiology, vol. 290, No. 3, Mar. 2019, pp. 649-657. (Year: 2019).*

Kevin T. Chen et al., "Ultra-Low-Dose 18F-Florbetaben Amyloid PET Imaging Using Deep Learning with Multi-Contrast MRI Inputs," Radiology, vol. 290, No. 3, Mar. 2019, pp. 649-657.

Ryohei Kuga et al., "Multi-task Learning Using Multi-modal Encoder-Decoder Networks with Shared Skip Connections," 2017 IEEE International Conference on Computer Vision Workshops (ICCVW), Oct. 22-29, 2017, pp. 403-411.

* cited by examiner

```
┌─────────────────────────────────────────────────────────────┐
│ providing an encoder and a decoder, and connecting layers   │──101
│ of the encoder with layers of the decoder by skip           │
│ connection to provide a U-Net type picture generator        │
└─────────────────────────────────────────────────────────────┘
                              │
                              ▼
┌─────────────────────────────────────────────────────────────┐
│ generating a group of generative adversarial networks by    │──102
│ matching a plurality of picture generators with a plurality │
│ of discriminators in one-to-one manner, in which the        │
│ plurality of picture generators use an input modality as a  │
│ conditional input and generating desired PET images as a    │
│ learning objective, the plurality of discriminators use an  │
│ input modality of a corresponding picture generator, a tag  │
│ image corresponding to the input modality, and an output    │
│ result as an input                                          │
└─────────────────────────────────────────────────────────────┘
                              │
                              ▼
┌─────────────────────────────────────────────────────────────┐
│ leaving the plurality of generative adversarial networks    │
│ in the group of the generative adversarial networks to      │
│ learn in parallel and leaving the picture generators of all │──103
│ the generative adversarial networks to share shallow        │
│ information to provide a first multi-task learning-type     │
│ generative adversarial network                              │
└─────────────────────────────────────────────────────────────┘
                              │
                              ▼
┌─────────────────────────────────────────────────────────────┐
│ evaluating parameters of the first multi-task learning-type │──104
│ generative adversarial network by using a standard-dose PET │
│ picture as a tag picture corresponding to the input         │
│ modality and using $L_1$ type loss function and cross       │
│ entropy loss function, and designing a joint loss function l│
│ for improving image quality according to output results of  │
│ the picture generators, the tag picture and the output      │
│ results of the discriminators                               │
└─────────────────────────────────────────────────────────────┘
                              │
                              ▼
┌─────────────────────────────────────────────────────────────┐
│ training the first multi-task learning-type generative      │──105
│ adversarial network according to the joint loss function l  │
│ in combination with an optimizer to provide a second        │
│ multi-task learning-type generative adversarial network     │
└─────────────────────────────────────────────────────────────┘
```

FIG. 1

METHOD AND SYSTEM FOR GENERATING MULTI-TASK LEARNING-TYPE GENERATIVE ADVERSARIAL NETWORK FOR LOW-DOSE PET RECONSTRUCTION

CROSS-REFERENCE TO RELATED APPLICATION

The present application is a continuation of international PCT application serial No. PCT/CN2020/135332 filed on Dec. 10, 2020. The entirety of the above-mentioned patent application is incorporated herein by reference and made a part of this specification.

BACKGROUND

Technical Field

The application relates to the field of deep learning technology, and in particular, to a method and a system for generating a multi-task learning-type generative adversarial network applied to the field of medical PET imaging.

Description of Related Art

Positron emission tomography (PET) is a functional imaging technique that uses radioactive substances known as radiotracers to visualize and measure changes in metabolic processes, and in other physiological activities including blood flow, regional chemical composition, and absorption. As the only new imaging technology that can display biomolecular metabolism, receptor, and neurotransmitter activity in vivo, PET has the characteristics of high sensitivity and specificity, which is suitable for the examination and adjuvant treatment of patients with tumor diseases, nervous system diseases and cardiovascular diseases.

Although PET scanning is non-invasive, it can expose an organism to ionizing radiation. A large amount of ionizing radiation is definitely harmful to the human body, especially for patients who need multiple examinations (such as tumor monitoring) or those who have a higher risk of cancers in the life cycle (such as pediatric patients). Almost all clinical and research applications need to improve image quality, but at the same time also need to minimize radiation exposure to reduce the risk associated with ionizing radiation. However, during PET imaging, reducing ionizing radiation will lead to low signal-to-noise ratio the reconstructed image and loss of image details.

SUMMARY

In order to address the problems of low signal-to-noise ratio and loss of image details in reconstructed low-dose PET images, the present application provides a method and a system for generating a multi-task learning-type generative adversarial network for low-dose PET reconstruction.

In a first aspect, the application provides a method and system for generating multi-task learning-type generative adversarial network for low-dose PET reconstruction, which adopts the following technical solutions.

A method for generating a multi-task learning-type generative adversarial network for low-dose PET reconstruction includes the steps of: providing an encoder and a decoder, and connecting layers of the encoder with layers of the decoder by skip connection to provide a U-Net type picture generator; generating a group of generative adversarial networks by matching a plurality of picture generators with a plurality of discriminators in one-to-one manner, in which the plurality of picture generators use an input modality as a conditional input and generating desired PET images as a learning objective, the plurality of discriminators use an input modality of a corresponding picture generator, a tag image corresponding to the input modality, and an output result as an input, and, in each group of the generative adversarial network, the input modality includes at least a low-dose PET image and an magnetic resonance (MR) image of a same picture object; leaving the plurality of generative adversarial networks in the group of the generative adversarial networks to learn in parallel and leaving the picture generators of all the generative adversarial networks to share shallow information to provide a first multi-task learning-type generative adversarial network; evaluating parameters of the first multi-task learning-type generative adversarial network by using a standard-dose PET picture as a tag picture corresponding to the input modality and using $L_1$ type loss function and cross entropy loss function, and designing a joint loss function 1 for improving image quality according to output results of the picture generators, the tag picture and the output results of the discriminators; and training the first multi-task learning-type generative adversarial network according to the joint loss function 1 in combination with an optimizer to provide a second multi-task learning-type generative adversarial network.

In the above technical solution, the encoder of the picture generator of the generative adversarial networks extracts features of a picture, and the decoder performs image reconstruction according to the features of the picture extracted by the encoder to obtain a reconstructed picture, and the discriminators judge true or false of a reconstructed picture output by the discriminators. Thereby, in the process of image reconstruction, low-dimensional and high-dimensional information can be greatly reused, and local and non-local information can be well fused, so as to enhance the performance of a traditional convolution operation and eliminate the noise of a reconstructed image to a large extent. Further, by means of leaving the plurality of generative adversarial networks in the group of the generative adversarial networks to learn in parallel and share shallow information to provide a first multi-task learning-type generative adversarial network, the first multi-task learning-type generative adversarial network can discriminate and reconstruct different types of images of the same picture object and continuously provide additional image details for a target picture to constructed, thereby reproducing the image details and reducing detail distortion to some extent. Finally, it facilitates addressing the problems of low signal-to-noise ratio and loss of detail in reconstructed low-dose PET images by training the first multi-task learning-type generative adversarial network according to the joint loss function 1 in combination with an optimizer to provide a second multi-task learning-type generative adversarial network.

Optionally, the step of designing a joint loss function 1 for improving image quality include: using a standard-dose PET picture as the tag picture corresponding to the input modality; evaluating parameters of the picture generators of the first multi-task learning-type generative adversarial network by using $L_1$ type loss function, and evaluating parameters of the discriminators of the first multi-task learning-type generative adversarial network by using a cross entropy loss function, so as to obtain a loss function $l_{L1}$ between output results of the picture generators and the tag picture and a loss function $l_{GAN}$ of the discriminators; and combining the loss function $l_{L1}$ and the loss function $l_{GAN}$ of all the generative adversarial networks to obtain the joint loss function 1.

In the above technical solution, by using a standard-dose PET picture as the tag picture corresponding to the input modality, a difference between the output results of the picture generators and the tag pictures measured by $L_1$ type loss function, namely, loss function $l_{L1}$, and a difference between the output results and the tag pictures measured by the cross entropy loss function, namely, loss function $l_{GAN}$, can be obtained. The difference can be measured for multiple times for the same output result to obtain a first multi-task learning-type joint loss function 1, which is helpful for improving the quality of reconstructed pictures (output images).

Optionally, the step of obtaining the joint loss function 1 includes: adding the loss function $l_{L1}$ to the loss function $l_{GAN}$ of a single generative adversarial network to provide a loss function output; and adding up the loss function outputs of all the generative adversarial networks of the first multi-task learning-type generative adversarial network to provide the joint loss function 1 of the first multi-task learning-type generative adversarial network.

In the above technical solution, adding the loss function $l_{L1}$ to the loss function $l_{GAN}$ enables a more sufficient evaluation of a difference between the output result (reconstructed image) and the tag picture, facilitating further addressing the problems of low signal-to-noise ratio and loss of detail in reconstructed low-dose PET images.

Optionally, the step of obtaining the joint loss function 1 includes: training the first multi-task learning-type generative adversarial network according to the joint loss function 1 in combination with an optimizer to provide a second multi-task learning-type generative adversarial network; and when the first multi-task learning-type generative adversarial network reaches a convergence state, determining the picture generators learning in parallel in the first multi-task learning-type generative adversarial network in the convergence state to be a second multi-task learning-type generative adversarial network.

In the above technical solution, by determining the picture generators learning in parallel in the first multi-task learning-type generative adversarial network in the convergence state to be a second multi-task learning-type generative adversarial network, the second multi-task learning-type generative adversarial network can steadily reconstruct the picture to obtain desired PET images.

Optionally, the discriminator includes a plurality of convolution layers and LearkyReLU activation functions, in which the convolution layer has a convolution kernel size of 3×3.

Optionally, both the encoder and the decoder include a plurality of basic blocks, and the basic blocks include a convolution layer, a batch-normalization layer, a dropout layer and a LearkyReLU activation function.

In a second aspect, the present application provides a system for generating a multi-task generative adversarial network for low-dose PET reconstruction, adopting the following technical solutions: a system for generating a multi-task generative adversarial network for low-dose PET reconstruction, including: a picture generator acquiring module, configured to connect layers of an encoder and layers of a decoder by skip connection to provide a U-Net type picture generator; an generative adversarial network generation module, configured to match a plurality of picture generators with a plurality of discriminators by one-to-one manner to provide a group of generative adversarial networks, in which the plurality of picture generators use an input modality as a conditional input and generating desired PET images as a learning objective, the plurality of discriminators use an input modality of a corresponding picture generator, a tag image corresponding to the input modality, and an output result as an input, and, in each group of the generative adversarial network, the input modality includes at least a low-dose PET image and an MR image of a same picture object; a first learning-type generative adversarial network acquiring module, configured to leave the plurality of generative adversarial networks in the group of the generative adversarial networks to learn in parallel and leave the picture generators of all the generative adversarial networks to share shallow information to provide a first multi-task learning-type generative adversarial network; a joint loss function acquiring module, configured to evaluate parameters of the first multi-task learning-type generative adversarial network by using a standard-dose PET picture as a tag picture corresponding to the input modality and using $L_1$ type loss function and cross entropy loss function, and design a joint loss function 1 for improving image quality according to output results of the picture generators, the tag picture and the output results of the discriminators; and a second multi-task leaning-type generative adversarial network acquiring module, configured to train the first multi-task learning-type generative adversarial network according to the joint loss function 1 in combination with an optimizer to provide a second multi-task learning-type generative adversarial network.

In the above technical solution, the picture generator acquiring module obtains a picture generator that is capable of extracting features of a picture and reconstructing the picture, and the generative adversarial network generation module obtains a group of general adversarial networks including a plurality of generative adversarial networks, so that the discriminator can make a judgement for the output results of the picture generators. Thereby, in the process of image reconstruction, low-dimensional and high-dimensional information can be greatly reused, and local and non-local information can be well fused, so as to enhance the performance of a traditional convolution operation and eliminate the noise of a reconstructed image to a large extent. Further, since the first learning-type generative adversarial network acquiring module leaves the plurality of generative adversarial networks in the group of the generative adversarial networks to learn in parallel and share shallow information to provide a first multi-task learning-type generative adversarial network, and continuously provide extra detail information for reconstruct target picture during picture reconstruction, details can be reproduced and distortion of details can be reduced to some extent. The joint loss function acquiring module use a standard-dose PET picture as a tag picture corresponding to the input modality and designing a joint loss function 1 by using $L_1$ type loss function and cross entropy loss function based on the first multi-task learning-type generative adversarial network. The second multi-task leaning-type generative adversarial network acquiring module trains the first multi-task learning-type generative adversarial network according to the joint loss function 1 in combination with an optimizer to provide a second multi-task learning-type generative adversarial network, so as to facilitate addressing the problems of low signal-to-noise ratio and loss of details in reconstructed low-dose PET images.

Optionally, the joint loss function acquiring module includes: a parameter designing sub-module, configured to use a standard-dose PET picture as a tag picture corresponding to the input modality; a loss function acquiring sub-module, configured to evaluate parameters of the picture generators of the first multi-task learning-type generative adversarial network by using $L_1$ type loss function and evaluate parameters of the discriminators of the first multi-task learning-type generative adversarial network by using a cross entropy loss function, so as to obtain a loss function $l_{L1}$ between output results of the picture generators and the tag picture and a loss function $l_{GAN}$ of the discriminators; and a joint loss function acquiring sub-module, configured to combine the loss function $l_{L1}$ and the loss function $l_{GAN}$ of all the generative adversarial networks to obtain the joint loss function 1.

In the above technical solution, by using a standard-dose PET picture as the tag picture corresponding to the input modality, a difference between the output results of the picture generators and the tag pictures measured by $L_1$ type loss function, namely, loss function $l_{L1}$, and a difference between the output results and the tag pictures measured by the cross entropy loss function, namely, loss function $l_{GAN}$, can be obtained. The difference can be measured for multiple times for the same output result to obtain a first multi-task learning-type joint loss function 1, which is helpful for addressing the problems of low signal-to-noise ratio and loss of detail in reconstructed low-dose PET images.

In a third aspect, the present application provides a computing device, including a memory, a processor, and a computer program stored in the memory and executable in the processor to perform any one of the methods in the first aspect.

In a fourth aspect, the present application provides a computer-readable storage medium storing a computer program capable of being loaded and executed by a processor to perform any one of the methods in the first aspect.

BRIEF DESCRIPTION OF THE DRAWINGS

FIG. 1 is a first flow chart of a method for generating a multi-task learning-type generative adversarial network for low-dose PET reconstruction according to an embodiment of the present application.

DESCRIPTION OF THE EMBODIMENTS

Figure 2:
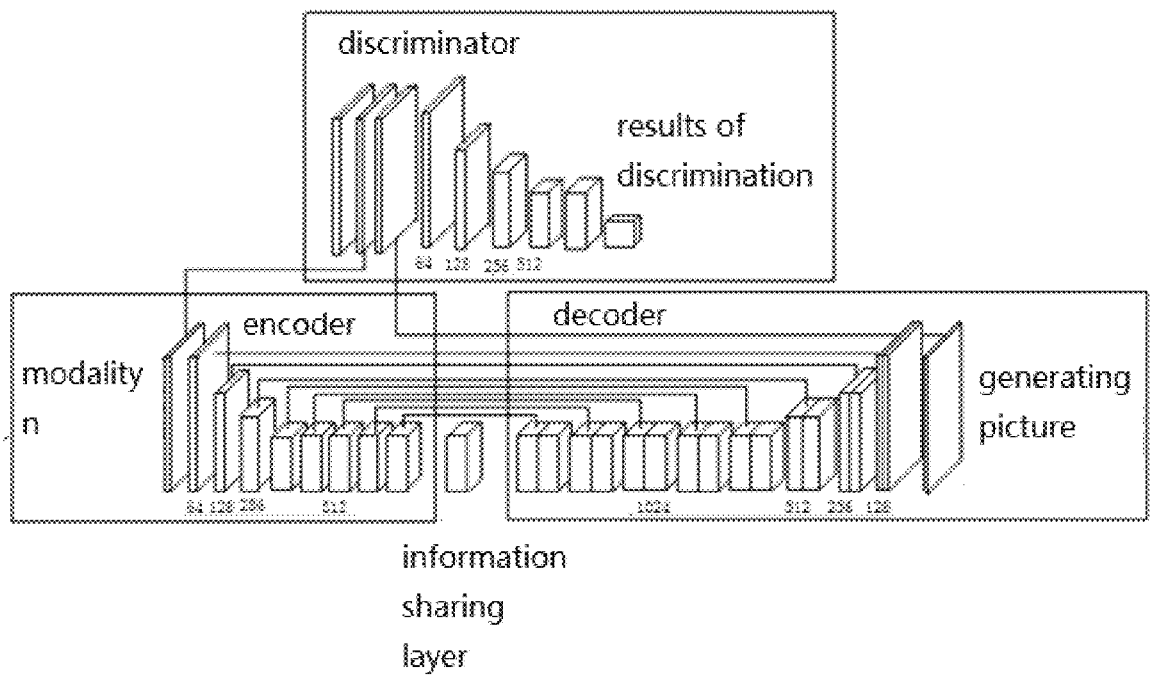
FIG. 2 is a structural diagram of a generative adversarial network according to an embodiment of the present application.

The present application is further described in detail with reference to FIGS. 1-6.

In 2019, an article "Ultra-Low-Dose 18F-Florbetaben Amyloid PET Imaging Using Deep Learning with Multi-Contrast MRI Inputs" was published by Kevin T. Chen et al in the Journal of Radiology, in which multi-modal MR images (T1, T2, t2FLAIR) were successfully applied for denoising low-dose PET images by using a U-net architecture encoder-decoder, in which MR images of three modalities and a low-dose PET image were input into the same encoder via different input channels. Each layer of the encoder performs two-dimensional convolution on the input cross (using a convolution kernel of 3×3) and completes batch normalization and overall streamlined unit activation operation, with a 2×2 maximum pool being used for reducing the dimensions of data. In the decoder part, the data in the encoder layer and the data in the decoder layer are stacked (U-Net structure) and linear interpolation is performed so as to restore the data to the original size for outputting. The network uses a corresponding standard-dose PET picture as a tag for training to get the final denoised PET image.

In 2017, "Multi-Task Learning Using Multi-Modal Encoder Decoder Networks With Shared Skip Connections" was published by Ryohei Kuga et al at IEEE International Computer Vision conference, which successfully applied multi-task learning to scene understanding. Their proposed multi-modal encoder-decoder network utilizes the multi-modal nature of multiple tasks to recognize scenes. Their encoder-decoder adopts a U-Net architecture, in which pictures of different modalities associated with each other are input, and, in addition to the shared latent representation among encoder-decoder pairs, the multi-modal encoder-decoder network model shares a skip connection from different encoders. By combining the two representation sharing mechanisms, the proposed method achieves a multi-task joint loss function for the whole network and efficiently learns a shared feature representation among all modalities in the training data.

Recently, the development of an integrated PET/MRI scanner provides more opportunities for algorithm-based image quality improving methods, especially for deep learning methods such as convolutional neural network (CNN). Because a PET/MRI scanner can obtain both structural and functional information in a single scanning session, more information can be used to promote a learning-based method, thereby improving image quality. MR images show high contrast between soft tissues. Therefore, MR images can provide structural information of soft tissues for guiding PET denoising. In particular, MRI refers to a magnetic resonance imaging.

A Generative Adversarial Network (GAN) is a deep learning model. The model has (at least) two modules in the framework, that is, a generation model and a judging model, and the game learning between the two models produces good output.

In the present application, a standard-dose PET image (picture) refers to a PET image (picture) that can meet the requirements of clinical diagnosis. On the contrary, a PET image (picture) that does not meet the requirements of clinical diagnosis is a low-dose picture. The standard dose and low dose will be different because of individual difference and drug difference, and the standards to meet the requirements of clinical diagnosis may also be different in different regions. However, it should be noted that, different users will have different demands and standards, so it can be set according to the demands and standards of a particular user.

An embodiment of the application provides a method for generating a multi-task learning-type generative network for low-dose PET reconstruction. Referring to FIG. 1 and FIG. 2, the generation method includes the following steps.

In step 101, an encoder and a decoder are provided, and layers of the encoder and layers of the decoder are connected by skip connection to provide a U-net type picture generator.

In particular, the picture generator is used for feature extraction and image reconstruction. Both the encoder and the decoder include basic blocks, and the basic blocks include convolution layer (a filter of 4×4), a batch normalization layer, a dropout layer and an activation layer (LearkyReLU). Each of the encoder and the decoder has 7 components in the form of the above basic blocks. The encoder (feature extraction network) extracts the features of input images, and the decoder (image reconstruction network) reconstructs the extracted feature. In such a network, a down-sampling layer is realized by a convolution having a step size of 2. Input images are passed through a series of layers in which the sampling is decreased by layers, until reaching a bottleneck layer, where the previous process will be reversed. That is, the encoder and the decoder require all information to pass through all layers including bottlenecks. Therefore, in order to avoid the picture generator from suffering from such information bottleneck to some extent, a skip connection is added adopting a general shape of "U-Net".

The basic block refers to a semantic sequence executed in sequence by a program.

In step 102, a plurality of picture generators are matched with a plurality of discriminators in one-to-one manner to provide a group of generative adversarial networks. The plurality of picture generators use an input modality as a conditional input to generate desired PET images as a learning objective. The plurality of discriminators use input modality of a corresponding picture generator, a tag picture corresponding to the input modality and an output result as input to provide a group of generative adversarial networks.

In particular, in each group of generative adversarial networks, the input modality of the picture generator at least includes two kinds of images of the same picture object: a low-dose PET image and an MR image. When the input modality is a low-dose PET image and an MR image, the low-dose PET image acts as the input of one picture generator, and the MR image acts as the input of another picture generator.

Learning object is an output result. In an embodiment of the discriminator, the discriminator includes six groups of convolution layers and LearkyReLU activation functions, in which the size of convolution kernel is 3×3. The last two layers of the discriminator are convolution layers, and the convolution has a step size of 2, to achieve a down-sampling layer. The discriminator is used to judge the true or false of output results (generated images) of the picture generator. The discriminator and the picture generator are trained and improved together, so that the images generated by the picture generator gradually become more and more accurate. Both the picture generator and the discriminator use an input modality as a conditional input, so that the reconstructed images have better quality.

It should be noted that, a desired PET image is set by a user according to their own actual demands, and the setting of the desired PET images can be performed by setting an indicator, including but not limited to, the signal-to-noise ratio of the desired PET image, the error between the desired PET image and the tag image, the similarity between the desired PET image and the tag image, or the like.

In step 103, the plurality of generative adversarial networks in a generative adversarial network group learn in parallel, and the picture generators of each of the generative adversarial networks share shallow information to provide a first multi-task learning-type generative adversarial network.

In particular, learning in parallel refers to a process of multi-task learning, which can be understood as a process for optimizing the parameters of the picture generator. By sharing the features between related tasks, an original task can be well summarized by the model, which is called a multi-task learning. The multi-task learning improves generalization performance by using domain knowledge contained in supervisory signals of related tasks. Therefore, the parameters of a picture generator are optimized by parallel learning in the process of the first multi-task learning-type generative adversarial network.

Figure 3:
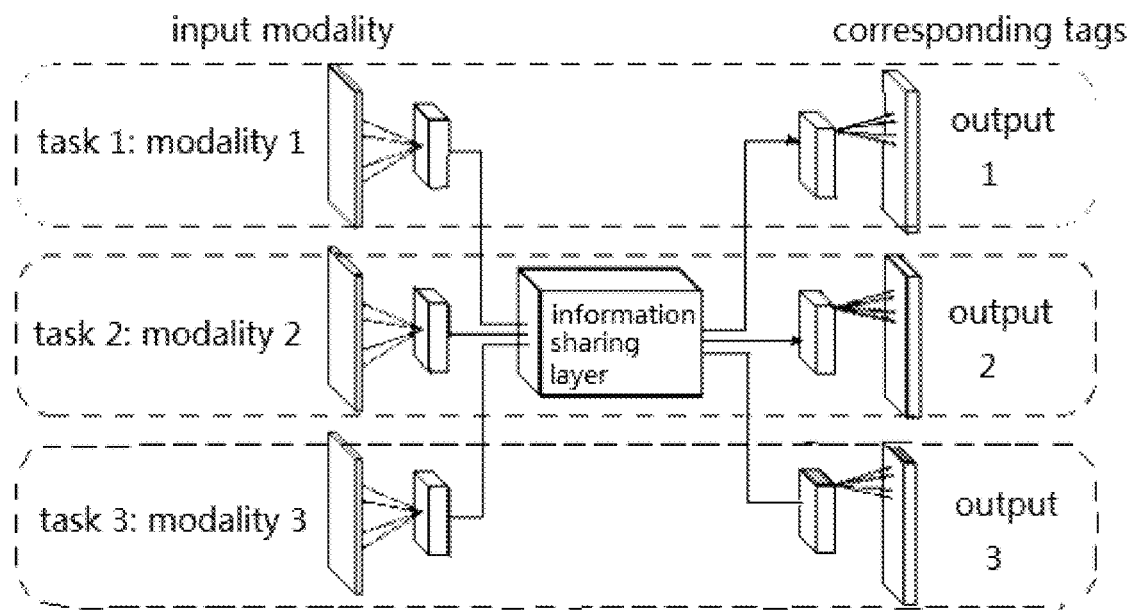
FIG. 3 is a first structural diagram of a first multi-task learning-type generative adversarial network according to an embodiment of the present application.

Referring to FIG. 3, it is to be noted that, in this embodiment, the first multi-task learning-type generative adversarial network includes three independent generative adversarial networks (independent tasks). That is, three generative adversarial networks are included in a group of generative adversarial networks, and the encoder and decoder of the picture generator communicate with an information sharing layer. A group of encoder-information sharing layer-decoder constitutes a separate channel, each of which mainly uses the picture generator to reconstruct a picture. All the picture generators share shallow information via the information sharing layer.

All the encoder/decoder pairs are connected via the information sharing layers. $X \in \{x_i, x_s, x_d\}$, representing as an input modality for each of the encoders; $E \in \{E_i, E_s, E_d\}$, representing the structure of the encoder, therefore, an output r, namely, a representation of the information sharing layer, $r \in \{E_i(x_i), E_s(x_s), E_d(x_d)\}$, for each of the encoders can be obtained. r from all the encoders has the same shape C×H×W (in which C, H, and W represent the number, height and width of channels, respectively). The structure of the decoder is defined as $D \in \{D_i, D_s, D_d\}$, and then $y \in \{D_i(r), D_s(r), D_d(r)\}$ is output. The information sharing layer between encoders and decoders are not distinguished among different modalities, i.e., the output of a decoder is fed into all decoders, and at the same time each decoder would have to decode the output of a decoder from any of the information sharing layer. In other words, an information sharing layer is shared for all encoder/decoder pairs.

In step 104, a standard-dose PET picture is used as a tag image corresponding to the input modality. An $L_1$ loss function and a cross entropy loss function are used to estimate the parameters of the first multi-task learning-type generative adversarial network. A joint loss function 1 for improving imaging quality is designed according to output result of the picture generators, the tag picture, and output results of the discriminators.

A group of pictures of different modalities (in this embodiment, modality 1, modality 2 and modality 3 correspond to a low-dose PET image, an MR image and another image of the same picture object) will be used as conditional inputs for individual independent tasks (generative adversarial network), in which another image can be a fusion image of PET and an MR images. The grouped pictures are associated with each other, namely, being a picture of the same object acquired via different image acquisition methods.

It should be noted that, essentially, the generative adversarial network (GAN) is a kind of special loss function, which can constantly approach a neural network through the game learning of discriminator models and generation discriminating model. $L_1$ type loss function, namely, $L_1$ norm loss function, also known as least absolute deviation (LAD) or least absolute error (LAE), is used for minimizing the sum of absolute differences between a target value and an estimator. A cross entropy is an important concept in Shannon's information theory. It is mainly used to measure the difference information between two probability distributions. Cross entropy can be used as a loss function in neural network (machine learning).

In step 105, the first multi-task learning-type generative adversarial network is trained to obtain a second multi-task learning-type generative adversarial network in combination with an optimizer according to the joint loss function 1.

It is worth noting that, the first multi-task learning-type generative adversarial network is trained continuously by using a group of pictures of a same picture object or paired pictures of different picture objects as input modalities, in combination with the optimizer and the joint loss function 1, until the first multi-task learning-type generative network reaches a convergent state, that is, the joint loss function 1 starts to be stable, with little fluctuation. Then, a plurality of the picture generators learning in parallel of the first multi-task learning-type generative adversarial network in the convergent state is determined as the second multi-task learning-type generative network, in which the plurality of picture generators learning in parallel share shallow information.

In other embodiments, when the first multi-task learning-type generative network is trained for a specified number of times, a second multi-task learning-type generative network can also be obtained.

The optimizer can be an Adam optimizer, momentum optimizer, etc.

In the above embodiment of a method for generating the multi-task learning-type generative adversarial network for low-dose PET reconstruction, the encoder of the picture generator of the generative adversarial networks extracts features of a picture, and the decoder performs image reconstruction according to the features of the picture extracted by the encoder to obtain a reconstructed picture, and the discriminators judge true or false of a reconstructed picture output by the discriminators. Thereby, in the process of image reconstruction, low-dimensional and high-dimensional information can be greatly reused, and local and non-local information can be well fused, so as to enhance the performance of a traditional convolution operation and eliminate the noise of a reconstructed image to a large extent. Further, by means of leaving the plurality of generative adversarial networks in the group of the generative adversarial networks to learn in parallel and share shallow information to provide a first multi-task learning-type generative adversarial network, the first multi-task learning-type generative adversarial network can discriminate and reconstruct different types of images of the same picture object and continuously provide additional image details for a target picture to constructed, thereby reproducing the image details and reducing detail distortion to some extent. Finally, it facilitates addressing the problems of low signal-to-noise ratio and loss of detail in reconstructed low-dose PET images by using a standard-dose PET picture as the tag picture corresponding to the input modality, designing a joint loss function in combination with the first multi-task learning-type generative adversarial network, and training the first multi-task learning-type generative adversarial network in combination with the optimizer to provide a second multi-task learning-type generative adversarial network.

Figure 4:
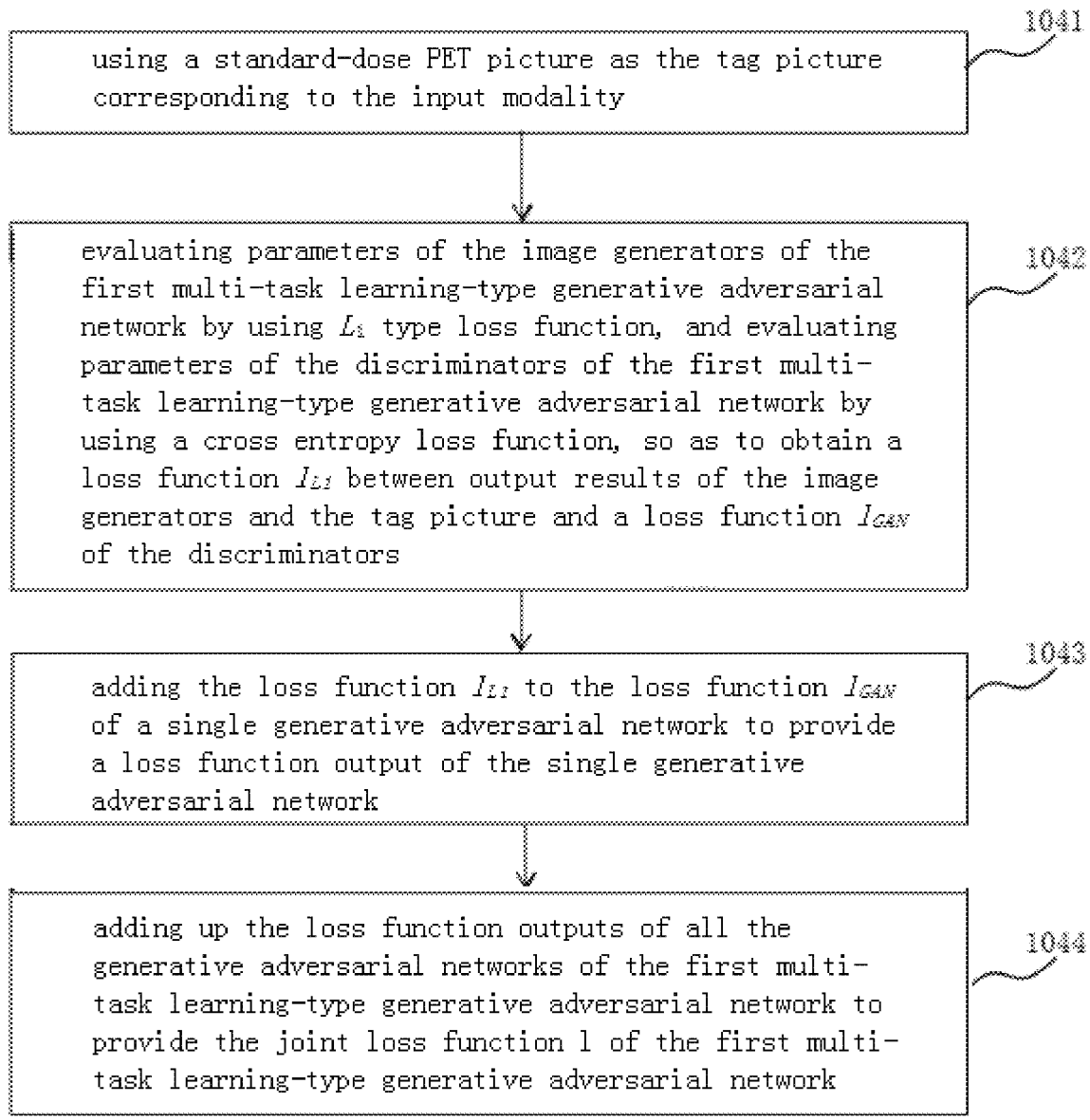
FIG. 4 is a second flow chart of a method for generating a multi-task learning-type generative adversarial network for low-dose PET reconstruction according to an embodiment of the present application.
Figure 5:
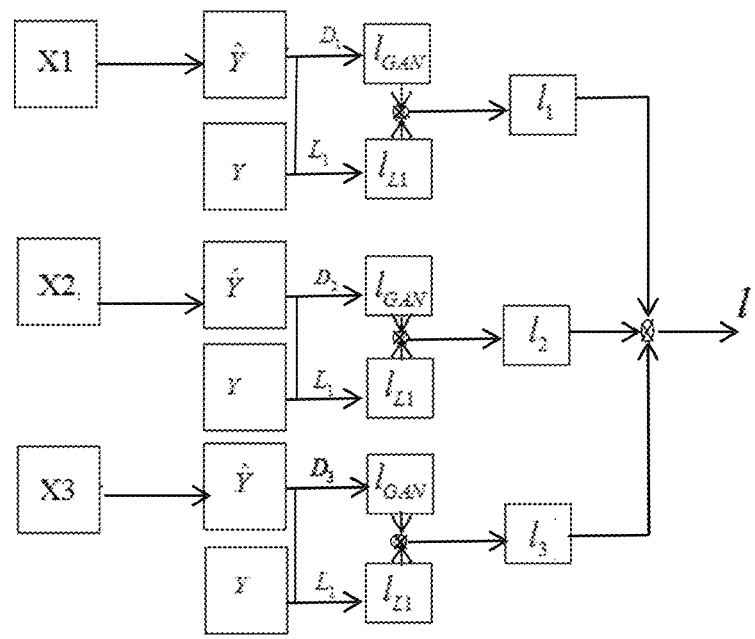
FIG. 5 is a second structural diagram of the first multi-task learning-type generative adversarial network according to an embodiment of the present application.

Referring to FIG. 4 and FIG. 5, an embodiment of designing the joint loss function 1 includes the following steps:

In step 1041, a standard-dose PET picture is used as a tag image corresponding to the input modality.

It should be noted that, two kinds of pictures, including but not less than a low-dose PET image and an MR image of the same image object are used as the input modalities of different picture generators.

In step 1042, an $L_1$ loss function is used to estimate parameters of the picture generator of the first multi-task learning-type generative adversarial network, and a cross entropy loss function is used to estimate parameters of the discriminator of the first multi-task learning-type generative adversarial network, to provide a loss function $l_{L1}$ between the output results of the picture generators and the tag picture, and a loss function $l_{GAN}$ of the discriminator.

It is to be noted that, loss function $l_{L1}$ and loss function $l_{GAN}$ can be obtained for each of the generative adversarial networks in the first multi-task learning-type generative adversarial network.

In this embodiment, the first multi-task learning-type generative adversarial network is a multi-task learning network with three-modality input (X1, X2, X3) and a single objective (Y), in which the single objective (Y) is also a tag picture. Therefore, a 3×1 network is to be simultaneously trained in the form of loss function sharing. Each of the generative adversary networks includes a generative adversary learning-type network (G, D), where G denotes a generator and D denotes a discriminator, with $L_1$ loss function ($L_1$ loss function can be used to learn low-dimensional features of an image, while GSN loss function can be used to better learn high-dimensional features of the image). In FIG. 5, D1, D2 and D3 denote the discriminators shown in FIG. 2.

Therefore, two separate loss functions $l_{L1}$ and loss function $l_{GAN}$ can be obtained for a single adversarial generating network. In particular, $$l_{GAN}(G,D)=E_{x,y}[\log D(x,y)]+E_x[\text{Log}(1-D(x,D(x,G(x))))] \quad (1),$$

$$l_{L1}(G)=E_{x,y}[\|y-G(x)\|_1] \quad (2),$$

where $E(\bullet)$ denotes expectation and $\|\bullet\|_1$ denotes norm of L1. X represents the input, that is, $X \in (X1, X2, X3)$, and y represents the output, that is, y is Ŷ.

Step 1043. The loss functions $l_{L1}$ is added to the loss function $l_{GAN}$ to provide the loss function output of a single generative adversarial network.

Step 1044. The outputs of the loss functions of all the generative adversarial networks of the first multi-task learning-type generative adversarial network was added up to obtain a joint loss function 1 of the first multi-task learning-type generative adversarial network.

In particular, $$1=\lambda_1(\lambda_{11}l_{GAN}(G,D)+\lambda_{12}l_{L1}(G))+\lambda_2(\lambda_{21}l_{GAN}(G,D)+\lambda_{22}l_{L2}(G))+\lambda_3(\lambda_{31}l_{GAN}(G,D)+\lambda_{32}l_{L3}(G)) \quad (3),$$

where $\lambda_1$, $\lambda_2$, and $\lambda_3$ are the weight coefficients of each generative adversarial network in the first multi-task learning-type generative adversarial network, $\lambda_{11}$, $\lambda_{12}$, $\lambda_{21}$, $\lambda_{22}$, $\lambda_{31}$, and $\lambda_{32}$ are the weight coefficients of corresponding loss functions in the generative adversarial networks. Further, in the process of training, the weight coefficients of the loss functions can be set according to the importance of different tasks, for example, setting a primary task or a secondary task. $\lambda_1(\lambda_{11}l_{GAN}(G,D)+\lambda_{12}l_{L1}(G))$ is the output of the loss function of a first generative adversarial network in which $l_1=\lambda_{11}l_{GAN}(G,D)+\lambda_{12}l_{L1}(G)$, $\lambda_2(\lambda_{21}l_{GAN}(G,D)+\lambda_{22}l_{L2}(G))$ is the loss function output of a second generative adversarial network in which $l_2=\lambda_{21}l_{GAN}(G,D)+\lambda_{22}l_{L2}(G)$, and $\lambda_3(\lambda_{31}l_{GAN}(G,D)+\lambda_{32}l_{L3}(G))$ is the loss function output of a third generative adversarial network in which $l_3=\lambda_{31}l_{GAN}(G,D)+\lambda_{32}l_{L3}(G)$.

In the test stage, a generator network (G1, G2, G3) obtained by training in any one of the task channels, or one having the best effect among them, can be used to realize the function of image reconstruction.

In the embodiment of the above design joint loss function 1, adding the loss function $l_{L1}$ to the loss function $l_{GAN}$ enables a more sufficient evaluation of a difference between the output result (reconstructed picture) and the tag picture, facilitating further addressing the problems of low signal-to-noise ratio and loss of detail in reconstructed low-dose PET images.

It should be noted that, the framework of the first multi-task learning-type generative adversarial network is not limited to three generative adversarial networks (more than or equal to two), and the adversarial generation network under the multi-task learning framework can alternatively use other types of networks (for example, recurrent neural network, deep belief network, deep reinforcement learning, convolutional neural network, etc.), or can use mixed networks of other types. The first multi-task learning-type generative adversarial network can be applied to the noise reduction of other types of medical images (MR images, CT images, etc.) after appropriate training changes. In addition to noise reduction, the method can also be applied to image segmentation, image classification and scene recognition after appropriate modifications.

Figure 6:
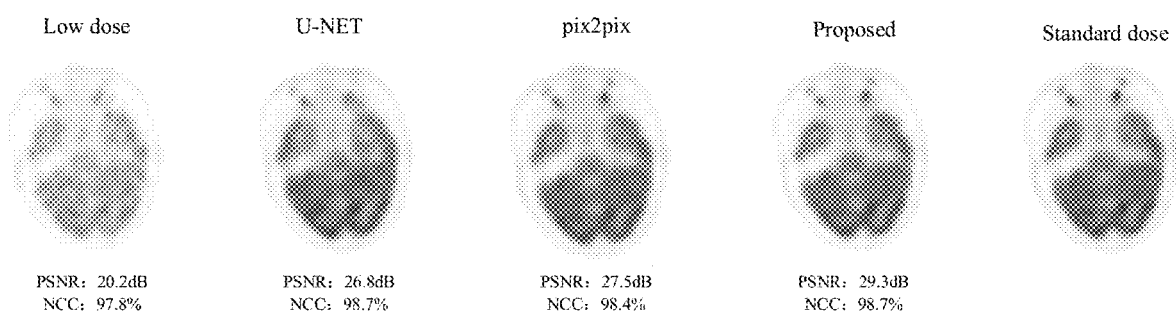
FIG. 6 is a PET image generated by a second multi-task learning-type generative adversarial network according to an embodiment of the application in comparison with the images generated by using other methods.

Referring to FIG. 6, in an actual test process, for the same original low-dose PET image, the reconstructed PET image obtained by the method using the U-Net network model, the reconstructed PET image obtained by using pix2pix method and the reconstructed PET image obtained by the second multi-task learning-type generative adversarial network in the application are compared with each other. In particular, (a) is an original low-dose PET picture, with a peak signal-to-noise ratio (PSNR) of 20.2 dB, NCC of 97.8%, and structural similarity (SSIM) of 65.8%. (b) is a PET picture reconstructed by using U-Net network model, with a peak signal to noise ratio (PSNR) of 26.8 dB, NCC of 98.7%, and SSIM of 95.7%. (c) is a picture reconstructed by using a pix2pix method, with a peak signal-to-noise ratio (PSNR) of 27.5 dB, NCC of 98.4%, and SSIM of 96.4%. (d) is the PET reconstruction image obtained by using the second multi-task learning-type generative adversarial network in the application, with a peak signal-to-noise ratio (PSNR) of 3 dB, NCC of 98.7%, and SSIM of 98.7%. (e) is a standard-dose PET picture. It can be concluded that, the method for reconstructing low-dose PET image by using the second multi-task learning-type generative adversarial network obtained in the application can effectively improve the peak signal-to-noise ratio and structural similarity of the images, while better restoring the image details to a certain extent.

In the present application, the generative adversarial network with conditional input can help restore the details of low-dose PET imaging, so as to improve the image quality.

Some embodiments of the present application further provide a system for generating a multi-task generative adversarial network for low-dose PET reconstruction. The system includes: a picture generator acquiring module, configured to connect layers of an encoder and layers of a decoder by skip connection to provide a U-Net type picture generator; an generative adversarial network generation module, configured to match a plurality of picture generators with a plurality of discriminators in one-to-one manner to provide a group of generative adversarial networks, in which the plurality of picture generators use an input modality as a conditional input and generating desired PET images as a learning objective, the plurality of discriminators use an input modality of a corresponding picture generator, a tag image corresponding to the input modality, and an output result as an input, and, in each group of the generative adversarial network, the input modality includes at least a low-dose PET image and an MR image of a same picture object; a first learning-type generative adversarial network acquiring module, configured to leave the plurality of generative adversarial networks in the group of the generative adversarial networks to learn in parallel and leave the picture generators of all the generative adversarial networks to share shallow information to provide a first multi-task learning-type generative adversarial network; a joint loss function acquiring module, configured to evaluate parameters of the first multi-task learning-type generative adversarial network by using a standard-dose PET picture as a tag picture corresponding to the input modality and using $L_1$ type loss function and cross entropy loss function, and design a joint loss function 1 for improving image quality according to output results of the picture generators, the tag picture and the output results of the discriminators; and a second multi-task leaning-type generative adversarial network acquiring module, configured to train the first multi-task learning-type generative adversarial network according to the joint loss function 1 in combination with an optimizer to provide a second multi-task learning-type generative adversarial network.

In the above embodiment, the picture generator acquiring module obtains a picture generator that is capable of extracting features of a picture and reconstructing the picture, and the generative adversarial network generation module obtains a group of general adversarial networks including a plurality of generative adversarial networks, so that the discriminator can make a judgement for the output results of the picture generators. Thereby, in the process of image reconstruction, low-dimensional and high-dimensional information can be greatly reused, and local and non-local information can be well fused, so as to enhance the performance of a traditional convolution operation and eliminate the noise of a reconstructed image to a large extent. Further, since the first learning-type generative adversarial network acquiring module leaves the plurality of generative adversarial networks in the group of the generative adversarial networks to learn in parallel and share shallow information to provide a first multi-task learning-type generative adversarial network, and continuously provides extra detail information for reconstruct target picture during picture reconstruction, details can be reproduced and distortion of details can be reduced to some extent. The joint loss function acquiring module uses a standard-dose PET picture as a tag picture corresponding to the input modality and designs a joint loss function 1 by using $L_1$ type loss function and cross entropy loss function based on the first multi-task learning-type generative adversarial network. The second multi-task leaning-type generative adversarial network acquiring module trains the first multi-task learning-type generative adversarial network according to the joint loss function 1 in combination with an optimizer to provide a second multi-task learning-type generative adversarial network, so as to facilitate addressing the problems of low signal-to-noise ratio and loss of details in reconstructed low-dose PET images.

As an embodiment of a joint loss function acquiring module, the joint loss function acquiring module includes: a parameter designing sub-module, configured to use a standard-dose PET picture as a tag picture corresponding to the input modality; a loss function acquiring sub-module, configured to evaluate parameters of the picture generators of the first multi-task learning-type generative adversarial network by using $L_1$ type loss function and evaluating parameters of the discriminators of the first multi-task learning-type generative adversarial network by using a cross entropy loss function, so as to obtain a loss function $l_{L1}$ between output results of the picture generators and the tag picture and a loss function $l_{GAN}$ of the discriminators; and a joint loss function acquiring sub-module, configured to combine the loss function $l_{L1}$ and the loss function $l_{GAN}$ of all the generative adversarial networks to obtain the joint loss function 1.

In the above embodiment of the joint loss function acquiring module, by using a standard-dose PET picture as the tag picture corresponding to the input modality, a difference between the output results of the picture generators and the tag pictures measured by $L_1$ type loss function, namely, loss function $l_{L1}$, and a difference between the output results and the tag pictures measured by the cross entropy loss function, namely, loss function $l_{GAN}$, can be obtained. The difference can be measured for multiple times for the same output result to obtain a first multi-task learning-type joint loss function 1, which is helpful for addressing the problems of low signal-to-noise ratio and loss of detail in reconstructed low-dose PET images.

Some embodiments of the present application further provide a computing device, including a memory, a processor, and a computer program stored in the memory and executable in the processor. When being executed in the processor, the computer program can perform any one of the methods for generating a multi-task learning-type adversarial network for low-dosage PET reconstruction.

Some embodiments of the present application further provide a computer-readable storage medium, which stores a computer program capable of being loaded and executed by a process to perform any one of the methods for generating a multi-task learning-type generative adversarial network for low-dose PET reconstruction. The computing devices can be a personal computer, a server, etc.

The computer-readable storage medium includes, for example, U-disk, mobile hard disk, read-only memory (ROM), random access memory (RAM), magnetic disk or optical disk and other media that can store program code.

What is claimed is:

1. A method for generating a multi-task learning-type generative adversarial network for low-dose positron emission tomography (PET) reconstruction, comprising steps of:
   providing an encoder and a decoder, and connecting layers of the encoder with layers of the decoder by skip connection to provide a U-Net type picture generator;
   generating a group of generative adversarial networks by matching a plurality of picture generators with a plurality of discriminators in one-to-one manner, wherein the plurality of picture generators use an input modality as a conditional input and generating desired PET images as a learning objective, the plurality of discriminators use an input modality of a corresponding picture generator, a tag image corresponding to the input modality, and an output result as an input, and, in each group of the generative adversarial network, the input modality comprises at least a low-dose PET image and an magnetic resonance (MR) image of a same picture object;
   leaving the plurality of generative adversarial networks in the group of the generative adversarial networks to learn in parallel and leaving the picture generators of all the generative adversarial networks to share shallow information to provide a first multi-task learning-type generative adversarial network;
   evaluating parameters of the first multi-task learning-type generative adversarial network by using a standard-dose PET picture as a tag picture corresponding to the input modality and using $L_1$ type loss function and cross entropy loss function, and designing a joint loss function 1 for improving image quality according to output results of the picture generators, the tag picture and the output results of the discriminators; and
   training the first multi-task learning-type generative adversarial network according to the joint loss function 1 in combination with an optimizer to provide a second multi-task learning-type generative adversarial network.

2. The method for generating a multi-task learning-type generative adversarial network for low-dose PET reconstruction according to claim 1, wherein the step of designing the joint loss function 1 for improving image quality comprises:
   using the standard-dose PET picture as the tag picture corresponding to the input modality;
   evaluating parameters of the picture generators of the first multi-task learning-type generative adversarial network by using $L_1$ type loss function, and evaluating parameters of the discriminators of the first multi-task learning-type generative adversarial network by using the cross entropy loss function, so as to obtain a loss function $l_{L1}$ between output results of the picture generators and the tag picture and a loss function $l_{GAN}$ of the discriminators; and
   combining the loss function $l_{L1}$ and the loss function $l_{GAN}$ of all the generative adversarial networks to obtain the joint loss function 1.

3. The method for generating a multi-task learning-type generative adversarial network for low-dose PET reconstruction according to claim 2, wherein the step of obtaining the joint loss function 1 comprises:
   adding the loss function $l_{L1}$ to the loss function $l_{GAN}$ of a single generative adversarial network to provide a loss function output; and
   adding up the loss function outputs of all the generative adversarial networks of the first multi-task learning-type generative adversarial network to provide the joint loss function 1 of the first multi-task learning-type generative adversarial network.

4. The method for generating a multi-task learning-type generative adversarial network for low-dose PET reconstruction according to claim 1, wherein the step of providing the second multi-task learning-type generative adversarial network comprises:
   training the first multi-task learning-type generative adversarial network according to the joint loss function 1 in combination with the optimizer; and
   when the first multi-task learning-type generative adversarial network reaches a convergence state, determining the picture generators learning in parallel in the first multi-task learning-type generative adversarial network in the convergence state to be the second multi-task learning-type generative adversarial network.

5. The method for generating a multi-task learning-type generative adversarial network for low-dose PET reconstruction according to claim 1, wherein the discriminator comprises a plurality of convolution layers and LearkyReLU activation functions, and the convolution layer has a convolution kernel size of 3×3.

6. The method for generating a multi-task learning-type generative adversarial network for low-dose PET reconstruction according to claim 1, wherein both the encoder and the decoder comprise a plurality of basic blocks, and the basic blocks comprise a convolution layer, a batch-normalization layer, a dropout layer and a LearkyReLU activation function.

7. A system for generating a multi-task learning-type generative adversarial network for low-dose positron emission tomography (PET) reconstruction, comprising:
- a picture generator acquiring module, configured to connect layers of an encoder and layers of a decoder by skip connection to provide a U-Net type picture generator;
- an generative adversarial network generation module, configured to match a plurality of picture generators with a plurality of discriminators by one-to-one manner to provide a group of generative adversarial networks, wherein the plurality of picture generators use an input modality as a conditional input and generating desired PET images as a learning objective, the plurality of discriminators use an input modality of a corresponding picture generator, a tag image corresponding to the input modality, and an output result as an input, and, in each group of the generative adversarial network, the input modality comprises at least a low-dose PET image and an magnetic resonance (MR) image of a same picture object;
- a first learning-type generative adversarial network acquiring module, configured to leave the plurality of generative adversarial networks in the group of the generative adversarial networks to learn in parallel and leave the picture generators of all the generative adversarial networks to share shallow information to provide a first multi-task learning-type generative adversarial network;
- a joint loss function acquiring module, configured to evaluate parameters of the first multi-task learning-type generative adversarial network by using a standard-dose PET picture as a tag picture corresponding to the input modality and using L1 type loss function and cross entropy loss function, and design a joint loss function 1 for improving image quality according to output results of the picture generators, the tag picture and the output results of the discriminators; and
- a second multi-task leaning-type generative adversarial network acquiring module, configured to train the first multi-task learning-type generative adversarial network according to the joint loss function 1 in combination with an optimizer to provide a second multi-task learning-type generative adversarial network.

8. The system for generating a multi-task learning-type generative adversarial network for low-dose PET reconstruction according to claim 7, wherein the joint loss function acquiring module comprises:
- a parameter designing sub-module, configured to use the standard-dose PET picture as a tag picture corresponding to the input modality;
- a loss function acquiring sub-module, configured to evaluate parameters of the picture generators of the first multi-task learning-type generative adversarial network by using $L_1$ type loss function and evaluate parameters of the discriminators of the first multi-task learning-type generative adversarial network by using the cross entropy loss function, so as to obtain a loss function $l_{L1}$ between output results of the picture generators and the tag picture and a loss function $l_{GAN}$ of the discriminators; and
- a joint loss function acquiring sub-module, configured to combine the loss function $l_{L1}$ and the loss function $l_{GAN}$ of all the generative adversarial networks to obtain the joint loss function 1.

\* \* \* \* \*